United States Patent
Randle et al.

(10) Patent No.: US 8,311,646 B2
(45) Date of Patent: Nov. 13, 2012

(54) MECHANISM FOR, AND METHOD OF, ATTACHING A LEAD CONDUCTOR CABLE TO A LEAD ELECTRODE

(75) Inventors: Matt Randle, El Cajon, CA (US); Ravi Jain, Austin, TX (US); Peter Fong, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/029,924

(22) Filed: Feb. 17, 2011

(65) Prior Publication Data

US 2011/0137392 A1    Jun. 9, 2011

Related U.S. Application Data

(62) Division of application No. 11/674,592, filed on Feb. 13, 2007, now Pat. No. 7,912,557.

(51) Int. Cl.
*A61N 1/05* (2006.01)
(52) U.S. Cl. .................................................. 607/119
(58) Field of Classification Search .......... 607/127–128, 607/115, 116, 119
See application file for complete search history.

(56) References Cited

U.S. PATENT DOCUMENTS

| 5,330,522 A | | 7/1994 | Kreyenhagen |
| 5,837,007 A | * | 11/1998 | Altman et al. ................. 607/127 |
| 6,766,203 B2 | * | 7/2004 | Doan et al. .................... 607/122 |

OTHER PUBLICATIONS

NonFinal Office Action, mailed Feb. 20, 2009—Parent U.S. Appl. No. 11/674,592.
Restriction Requirement, mailed Nov. 30, 2009—Parent U.S. Appl. No. 11/674,592.
Final Office Action, mailed Mar. 30, 2010—Parent U.S. Appl. No. 11/674,592.
Notice of Allowance, mailed Jan. 20, 2011—Parent U.S. Appl. No. 11/674,592.

* cited by examiner

*Primary Examiner* — Scott Getzow
*Assistant Examiner* — Amanda Patton

(57) ABSTRACT

A cardio electrotherapy lead is disclosed herein. In one embodiment, the lead includes a tubular body, a conductor cable and an electrode. The conductor cable longitudinally extends through the tubular body and includes a distal end. The electrode is located on the tubular body and includes an attachment mechanism mechanically coupling the lead distal end to the electrode.

10 Claims, 3 Drawing Sheets

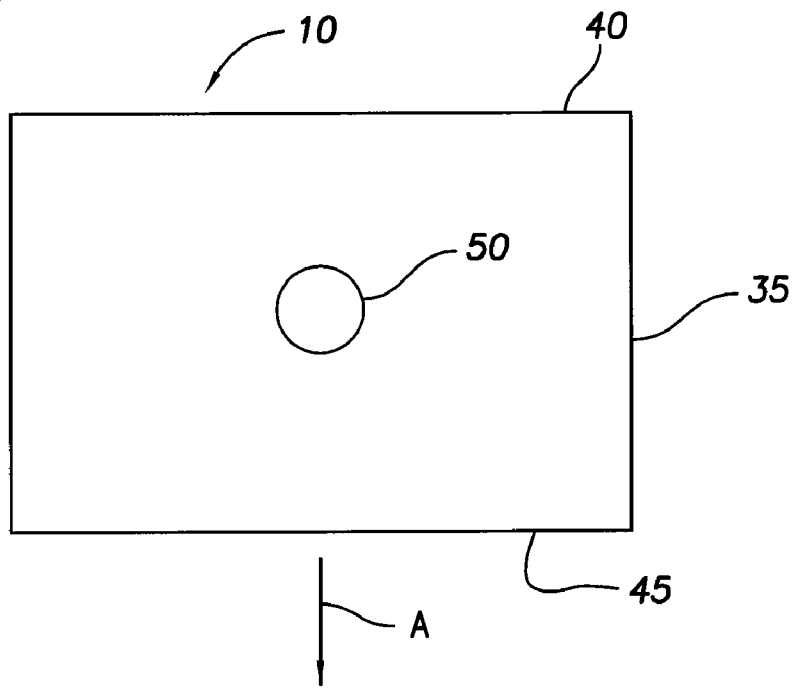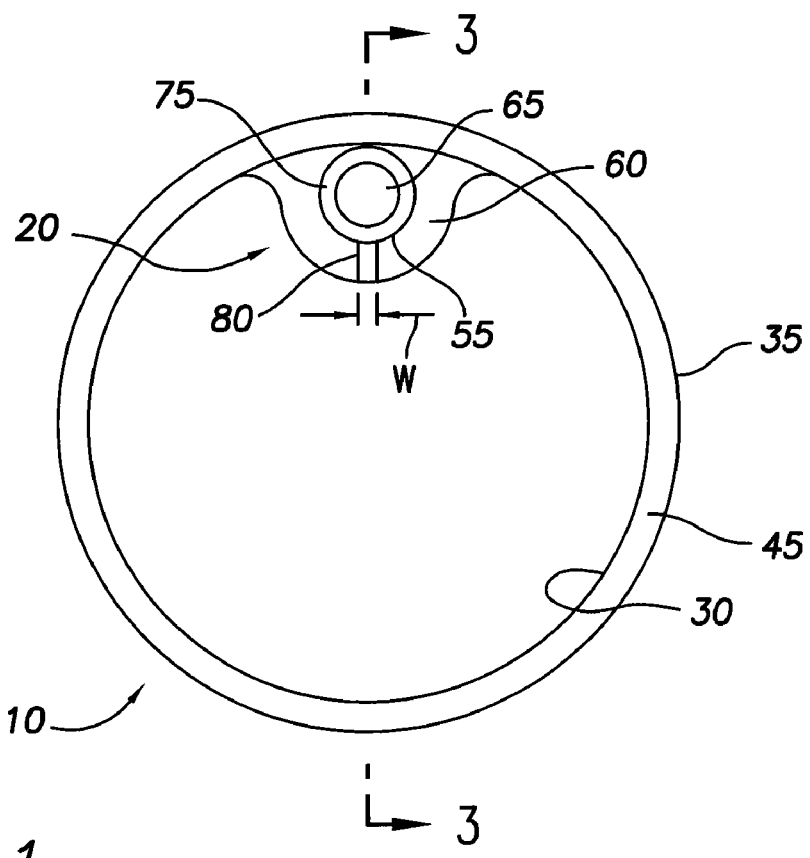

MECHANISM FOR, AND METHOD OF, ATTACHING A LEAD CONDUCTOR CABLE TO A LEAD ELECTRODE

CROSS REFERENCE TO RELATED APPLICATIONS

This application is a division of U.S. patent application Ser. No. 11/674,592, filed Feb. 13, 2007.

FIELD OF THE INVENTION

The present invention relates cardio electrotherapy leads and methods of manufacturing such leads. More particularly, the present invention relates to mechanisms for, and methods of, attaching a lead cable conductor to a lead electrode.

BACKGROUND OF THE INVENTION

Leads for administering cardio electrotherapy (e.g., pacing and/or defibrillation) have tubular bodies with electrodes forming a portion of the circumferential outer surface of the lead and/or a portion of the distal end of the lead. The electrodes are used for sensing, pacing and/or defibrillation. Electrodes for over-the-wire leads come in a variety of shapes including rings, coils, studs/bumps, helical spring tips, etc. Regardless of the shape of the electrode, the electrode must be electrically hardwired to a conductor cable extending through the lead body from the pacemaker and/or defibrillator.

It is clinically advantageous to decrease the size of electrodes to improve trackability over guidewires and to lower sensing, pacing and defibrillation thresholds through higher current densities. For example, with respect to ring electrodes, the length of the ring electrode along the longitudinal length of the lead body is shortened to improve trackability and raise current density.

Conductor cables have typically been electrically hardwired to electrodes via welding the cable directly to the electrode or using a short crimp slug welded to the electrode. These methods of hardwiring a cable to an electrode have several disadvantages. First, the weld zone of the cable and the electrode has a decreased fatigue life. Second, the cable can withstand only a reduced pull force due to the reduced/compressed length of a short crimp slug. Third, the methods increase the complexity of tooling and manufacturing. Fourth, as it is advantageous from a manufacturing perspective to minimize the profile of a cable to electrode attachment to aid assembly, the magnitude of the three preceding disadvantages is increased.

There is a need in the art for an attachment configuration and a method of attachment that facilitates the ease of connection between a cable conductor and a lead electrode. There is also a need in the art for an attachment configuration and a method of attachment that increases the integrity of a connection between a cable conductor and a lead electrode.

SUMMARY

A cardio electrotherapy lead is disclosed herein. In one embodiment, the lead includes a tubular body, a conductor cable and an electrode. The conductor cable longitudinally extends through the tubular body and includes a distal end. The electrode is located on the tubular body and includes an attachment mechanism mechanically coupling the lead distal end to the electrode.

A method of manufacturing a cardio electrotherapy lead is disclosed herein. In one embodiment, the method includes mechanically attaching a distal end of a cable conductor of the lead to an electrode of the lead.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is a distal end elevation of the electrode.

FIG. 2 is a top plan view of the electrode as viewed from the direction of arrow A in FIG. 1.

DETAILED DESCRIPTION

The present application describes a system and method for coupling an electrode 10 for a cardio electrotherapy lead to a cable conductor 15 extending through the lead. The electrode 10 has an attachment mechanism 20 integral to the electrode 10. The attachment mechanism 20 is configured to receive and snap-fit/compression-fit/friction-fit with an attachment feature 25 of the cable conductor 15 to couple the cable conductor 15 to the electrode 10.

The system and method for coupling the electrode 10 to the cable conductor 15 is advantageous for at least the following reasons. First, the system and method simplifies the process involved with forming a connection between the cable conductor 15 and the electrode 10. Second, the system and method increases the reliability of the connection formed between the cable conductor 15 and the electrode 10.

Figure 3:
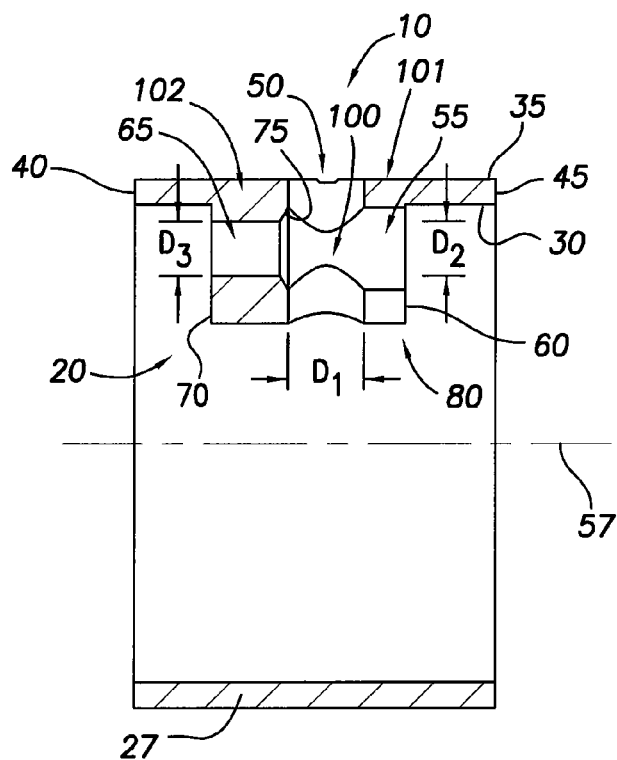
FIG. 3 is a sectional view of the electrode as taken along section line 3-3 in FIG. 1.
Figure 4:
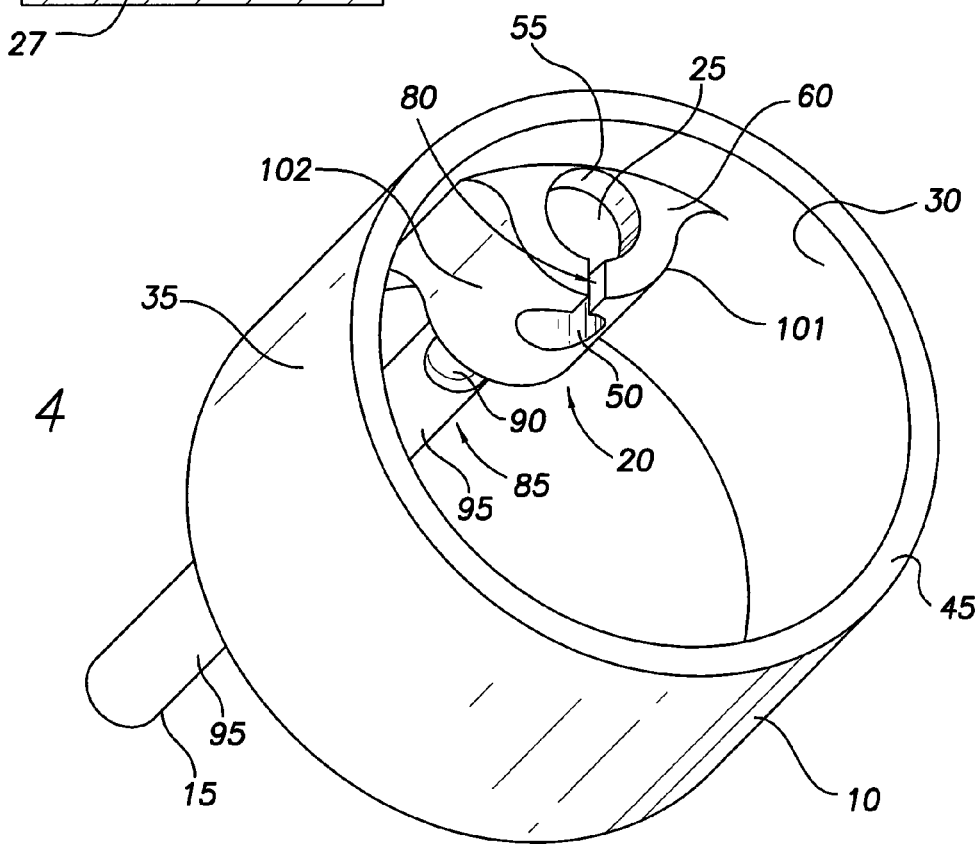
FIG. 4 is a distal end isometric view of the electrode coupled to the cable conductor 15.
Figure 5:
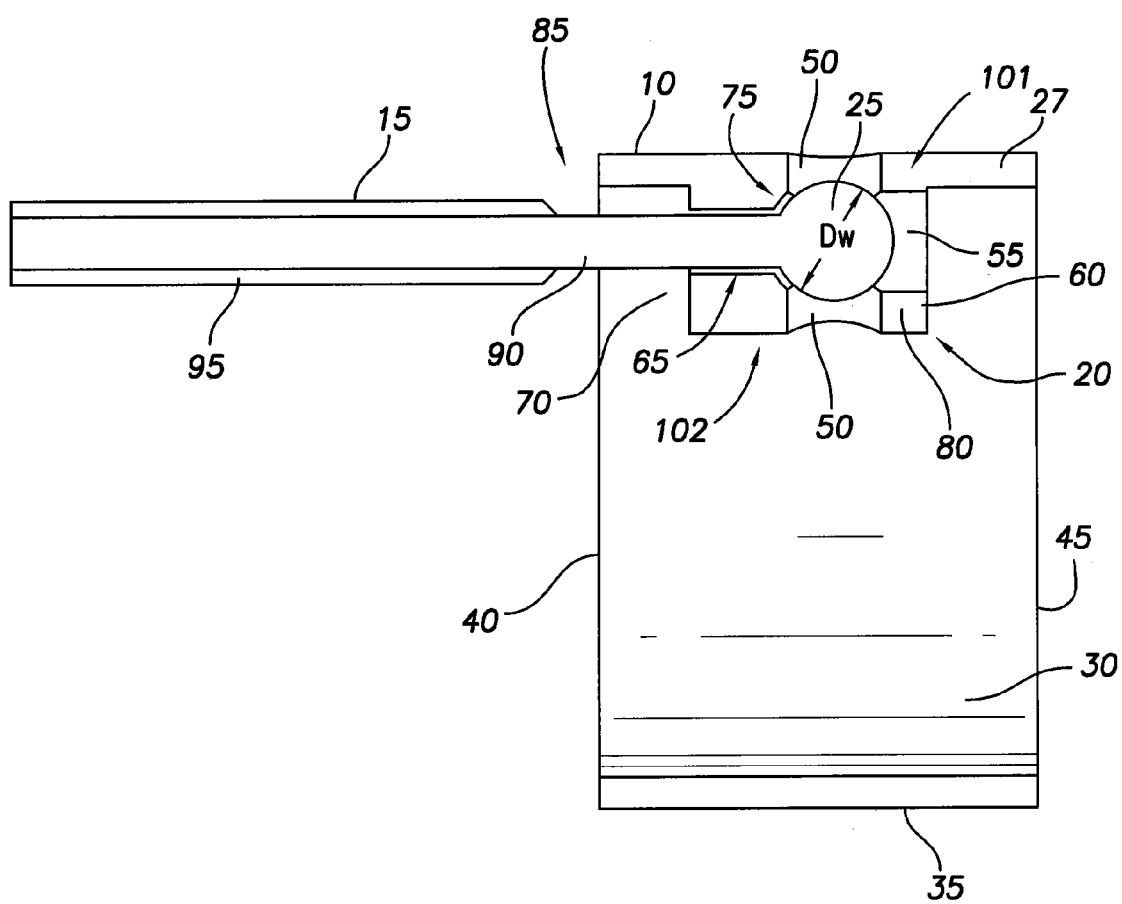
FIG. 5 is a sectional view of the electrode coupled to the cable conductor as taken along section line 3-3 in FIG. 1.

For a detailed discussion of the system and method of coupling an electrode 10 to a cable conductor 15, reference is made to FIGS. 1-5. FIG. 1 is a distal end elevation of the electrode 10. FIG. 2 is a top plan view of the electrode as viewed from the direction of arrow A in FIG. 1. FIG. 3 is a sectional view of the electrode 10 as taken along section line 3-3 in FIG. 1. FIG. 4 is a distal end isometric view of the electrode 10 coupled to the cable conductor 15. FIG. 5 is a sectional view of the electrode 10 coupled to the cable conductor 15 as taken along section line 3-3 in FIG. 1.

As depicted in FIGS. 1-5, in one embodiment, the electrode 10 is a ring electrode 10 having a cylindrical wall 27 with an inner circumferential surface 30, an outer circumferential surface 35, a proximal edge 40, and a distal edge 45. When the ring electrode 10 is mounted on the tubular body of a lead, the inner circumferential surface 30 extends about the circumference of the tubular body, the outer circumferential surface 35 forms a portion of the outer circumferential surface of the of the lead tubular body, the proximal edge 40 faces towards the proximal end of the lead tubular body, and the distal edge 45 faces towards the distal end of the lead tubular body.

As shown in FIGS. 1 and 3-5, the attachment mechanism 20 is a portion of the electrode cylindrical wall 27 that protrudes radially inward from the inner circumferential surface 30 of the cylindrical wall 27. In one embodiment, the attachment mechanism 20 appears as approximately two-thirds to three-quarters of a cylinder protruding radially inward from the inner circumferential surface 30 of the cylindrical wall 27. In other embodiments, the attachment mechanism 20 will have other appearances.

As indicated in FIGS. 2 and 3, in one embodiment, the attachment mechanism 20 includes a radial hole 50 that is centered transversely relative to a longitudinal center axis of the attachment mechanism 20 and extends radially completely through the cylindrical wall 27 and the attachment mechanism 20. In other words, as depicted in FIG. 3, the radial hole 50 daylights completely through the outer circumferential surface 35 of the cylindrical wall 27 and the most radially inward surface of the attachment mechanism 20.

As shown in FIGS. 1 and 3, in one embodiment, the attachment mechanism 20 includes a proximally extending hole 55 that is centered such that its center axis coincides with the center axis of the radial hole 50. The center axis of the proximally extending hole 55 is parallel to the longitudinal axis 57 of the electrode ring 10. The proximally extending hole 55 extends proximally from the distal face 60 of the attachment mechanism 20 and through the radial hole 50 until reaching the proximal wall of the radial hole 50.

As indicated in FIGS. 1 and 3, in one embodiment, the attachment mechanism 20 includes a distally extending hole 65 that is centered such that it is coaxially oriented relative to the proximally extending hole 55. Thus, the center axis of the distally extending hole 65 is parallel to the longitudinal axis 57 of the electrode ring 10. The distally extending hole 65 extends distally from the proximal face 70 of the attachment mechanism 20 until reaching the proximal wall of the radial hole 50 where the distally extending hole 65 transitions via a chamfer 75 to nearly the diameter of the of the proximally extending hole 55.

As shown in FIGS. 1, 3 and 4, a slot 80 extends radially towards the longitudinal center axis 57 of the electrode ring 10 from the inner circumferential surface of the proximally extending hole 55. The slot 80 also extends distally from the circumferential surface of the radial hole 50 to the distal face 60 of the attachment mechanism 20. Thus, as can be understood from FIG. 4, the circumferential surface of the proximally extending hole 55 can expand via the slot 80 to allow the attachment feature 25 of the conductor cable 15 to be received at the intersection of the holes 50, 55, 65, as shown in FIG. 5.

As shown is FIGS. 4 and 5, the distal end 85 of the conductor cable 15 couples with the electrode 10. The conductor cable 15 extends through the lead body between the electrode 10 and the proximal end of the lead. The conductor cable 15 includes a conductive core 90 and an electrically insulative jacket 95 extending about the core 90. The jacket 95 terminates as it nears the distal end of the conductor cable 15, thereby exposing the core 90. The core 90 extends distally from the termination of the jacket 95 to terminate at its extreme distal end as the attachment feature 25. In one embodiment, the attachment feature 25 is ball-like in shape. In other embodiments, the attachment feature 25 has other shapes (e.g., cylinder-like, egg-like, etc.).

In one embodiment, the core 90 and its attachment feature 25 are formed from stainless steel, platinum, platinum-iridium, gold, MP35N, etc. In one embodiment, the jacket 95 is formed from a polymer material such as ETFE, silicone, parylene, etc.

As illustrated in FIGS. 4 and 5, the conductor cable 15 couples to the electrode 10 by the attachment feature 25 being received in the attachment mechanism 20 such that the ball-like attachment feature 25 occupies the intersection 100 of the holes 50, 55, 65. The proximal side of the ball-like attachment feature 25 seats against the chamfer or seat 75 and the core 90 extends distally therefrom through the distally extending hole 65.

As can be understood from FIGS. 4 and 5, when the attachment feature 25 is received in the attachment mechanism 20, the attachment feature 25 occupies the space 100 between a distal entry portion 101 of the attachment mechanism and a proximal backstop portion 102 of the attachment mechanism. The distal entry portion 101 is configured to allow the attachment feature 25 to enter the attachment mechanism 20 and prevent distal displacement of the attachment feature 25 once it has been received within the attachment mechanism 20. The proximal backstop portion 102 prevents further proximal displacement of the attachment feature 25 once received within the attachment mechanism 20.

As can be understood from FIGS. 1 and 3-5, to cause the ball-like attachment feature 25 to be received in the attachment mechanism 25, the proximal end of the conductor cable 15 is proximally fed through the proximally extending hole 55, the intersection 100 and the distally extending hole 65. The conductor cable 15 continues to be fed proximally until the ball-like attachment feature 25 abuts against the entrance of the proximally extending hole 55 at the distal face 60 of the attachment mechanism 20. The conductor cable 15 is further proximally fed such that the sides of the slot 80 are forced apart to increase the diameter of the proximally extending hole 50 to accommodate the larger diameter ball-like attachment feature 25. In other words, the proximally extending hole 50 deforms via the expansion of the slot 80 to allow the ball-like attachment feature 25 to pass through the proximally extending hole 50.

Once the ball-like attachment feature 25 passes through the proximally extending hole 55 and occupies the intersection 100, the proximally extending hole 50 snaps or otherwise returns to its non-deformed state, thereby preventing the larger diameter ball-like attachment feature 25 from distally exiting out of the attachment mechanism 20. Once the ball-like attachment feature 25 occupies the intersection 100, the attachment feature 25 seats against the chamfer or seat 75. Further proximal displacement of the attachment feature 25 is prevented because the diameter of the ball-like attachment feature 25 exceeds the diameter of the distally extending hole 65 and the distally extending hole 65 will not deform as the proximally extending hole 55.

As can be understood from FIGS. 4 and 5, the attachment mechanism 20 provides a friction-fit/snap-fit/compression-fit type of attachment to the attachment feature 25 of the conductor cable 15. Thus, a conductor cable 15 can be quickly, easily and securely coupled to an electrode 10. The attachment mechanism 20 provides a low profile attachment configuration that does not have the stress issues associated with welding.

In one embodiment, the radial hole 50 has a diameter $D_1$ of between approximately 0.002 inch and approximately 0.025 inch, the proximally extending hole 55 has a diameter $D_2$ of between approximately 0.003 inch and approximately 0.020 inch, the distally extending hole 65 has a diameter $D_3$ of between approximately 0.002 inch and approximately 0.015 inch, the slot 80 has a width W of between approximately 0.001 inch and approximately 0.015 inch, and the attachment feature 25 has a diameter $D_4$ of between approximately 0.003 inch and approximately 0.025 inch.

In one embodiment, the diameter $D_4$ of the ball-like attachment feature 25 is between: approximately 10 percent and approximately 40 percent larger than the diameter $D_1$ of the radial hole 50; approximately 5 percent and approximately 20 percent larger than the diameter $D_2$ of the proximally extending hole 55 when the proximally extending hole 55 is in the unexpanded or non-deformed state; and approximately 10 percent and approximately 90 percent larger than the diameter $D_3$ of the distally extending hole 65, which is large enough to allow the proximal passage of the conductor cable 65.

In one embodiment, the chamfer 75 is made at an angle of between approximately 10 degrees and approximately 60 degrees relative to the center axis of the distally extending hole 65. Thus, the chamfer 75 generally matches the outer circumferential surface of the ball-like attachment feature 25 and serves as a seat 75 for the ball-like attachment feature 25.

In one embodiment, the attachment mechanism 20 is an integral portion of the electrode 10. In one embodiment, the attachment mechanism 20 is cast, machined or otherwise formed with the electrode 10.

While the system and method of coupling an electrode 10 to a cable conductor 15 is described above with respect to the electrode 10 being a ring electrode, in other embodiments, as readily understandable by those skilled in the art, the electrode 10 will have other configurations without departing from the spirit of the invention disclosed herein. For example, in other embodiments, the electrode 10 is a helical coil, stud-shaped, crescent (half ring), etc.

Although the present invention has been described with reference to preferred embodiments, persons skilled in the art will recognize that changes may be made in form and detail without departing from the spirit and scope of the invention.

What is claimed is:

1. A cardio electrotherapy lead comprising: a tubular body including a proximal end and a distal end; a conductor cable extending through the tubular body and including an attachment feature; and a ring electrode located on the tubular body and including means for receiving the attachment feature, the means for receiving including a proximal bore configured to pass the conductor cable but not the attachment feature.

2. The lead of claim 1, wherein the means for receiving further includes a distal bore configured to pass the attachment feature.

3. The lead of claim 2, wherein the distal bore is configured to resiliently expand to pass the attachment feature.

4. The lead of claim 3, wherein the means for receiving includes a slot in communication with the distal bore that allows the distal bore to resiliently expand.

5. The lead of claim 1, wherein the means for receiving is at least partially defined by a wall of the ring electrode.

6. The lead of claim 5, wherein at least part of the means for receiving extends from the wall of the ring electrode.

7. The lead of claim 6, wherein the part of the means for receiving extends toward a longitudinal axis of the tubular body.

8. The lead of claim 1, wherein the ring electrode has a cylindrical wall with an inner circumferential surface, an outer circumferential surface, a proximal edge, and a distal edge.

9. The lead of claim 8, wherein when the ring electrode is mounted on the tubular body, the inner circumferential surface extends about the circumference of the tubular body, the outer circumferential surface forms a portion of the outer circumferential surface of the tubular body, the proximal edge faces towards the proximal end of the lead body, and the distal edge faces towards the distal end of the tubular body.

10. The lead of claim 1, wherein the means for receiving includes a snap-fit, compression-fit, or friction-fit of the attachment feature.

\* \* \* \* \*